United States Patent [19]

Conti

[11] Patent Number: 4,842,418
[45] Date of Patent: Jun. 27, 1989

[54] TWO TEMPERATURE MEASURING PROBE

[75] Inventor: Richard Conti, Holland, Pa.

[73] Assignee: Electro-Nite Company, Philadelphia, Pa.

[21] Appl. No.: 273,614

[22] Filed: Nov. 17, 1988

Related U.S. Application Data

[63] Continuation of Ser. No. 929,232, Nov. 10, 1986, abandoned.

[51] Int. Cl.[4] .................. G01N 25/04; G01K 1/14
[52] U.S. Cl. .................. 374/139; 73/DIG. 9; 73/864.58; 374/26; 374/166
[58] Field of Search .............. 374/26, 139, 140, 16, 374/166; 73/864.53, 864.55, DIG. 9; 136/234

[56] References Cited

U.S. PATENT DOCUMENTS

| | | | |
|---|---|---|---|
| 3,374,122 | 3/1968 | Cole | 374/140 X |
| 3,455,164 | 7/1969 | Boyle | 374/26 |
| 3,481,201 | 12/1969 | Falk . | |
| 3,559,452 | 2/1971 | Perbix et al. | 374/26 |
| 3,577,886 | 5/1971 | Wiese . | |
| 3,643,509 | 2/1972 | Surinx . | |
| 3,656,338 | 4/1972 | Collins . | |
| 3,656,346 | 4/1972 | Collins . | |
| 3,709,040 | 1/1973 | Coe | 374/26 |
| 3,748,908 | 7/1973 | Falk . | |
| 3,915,002 | 10/1975 | Hance et al. | 374/140 X |
| 3,922,916 | 12/1975 | Wickert | 374/140 |
| 4,069,715 | 1/1978 | Falk | 374/140 |
| 4,102,197 | 7/1978 | Bardenheuer . | |
| 4,182,181 | 1/1980 | Arvai . | |
| 4,401,389 | 8/1983 | Theuwis . | |

FOREIGN PATENT DOCUMENTS

| | | | |
|---|---|---|---|
| 1585434 | 12/1970 | France | 73/864.53 |
| 30913 | 3/1983 | Japan . | |

*Primary Examiner*—Daniel M. Yasich
*Attorney, Agent, or Firm*—Panitch, Schwarze, Jacobs and Nadel

[57] ABSTRACT

A device for measuring both the phase change temperature of a sample of a molten metal bath and the actual bath temperature by means of a single thermocouple. The device having a chamber defined by a housing such that the housing will be consumed by the molten metal bath after determination of the phase change temperature of the sample within the chamber. After consumption of the housing, the sample remelts into the bath and the thermocouple determines the bath temperature.

12 Claims, 4 Drawing Sheets

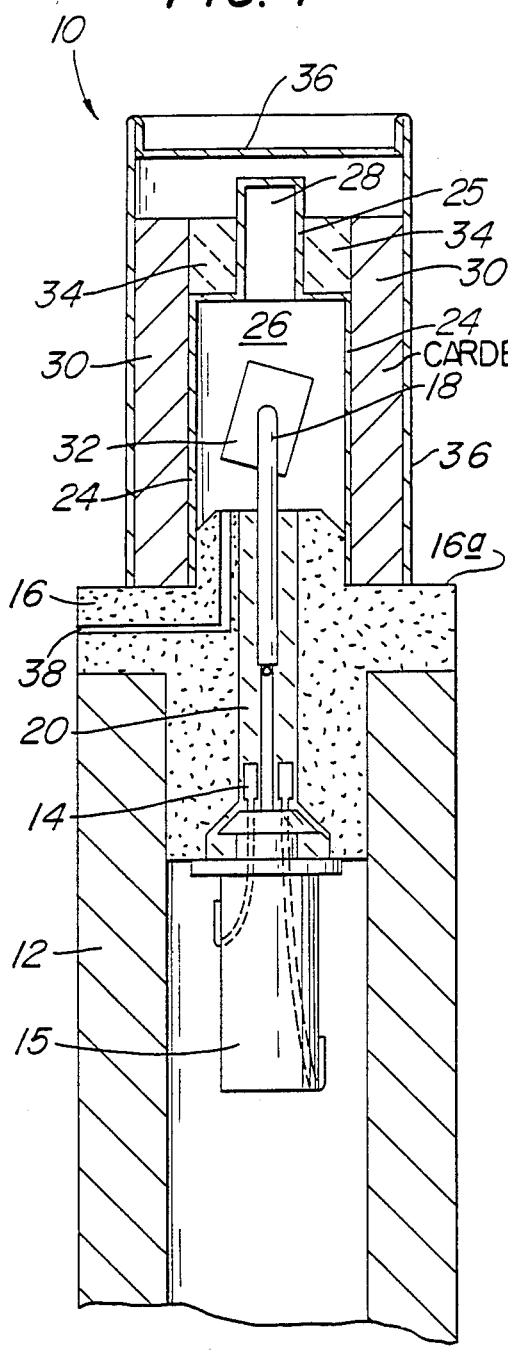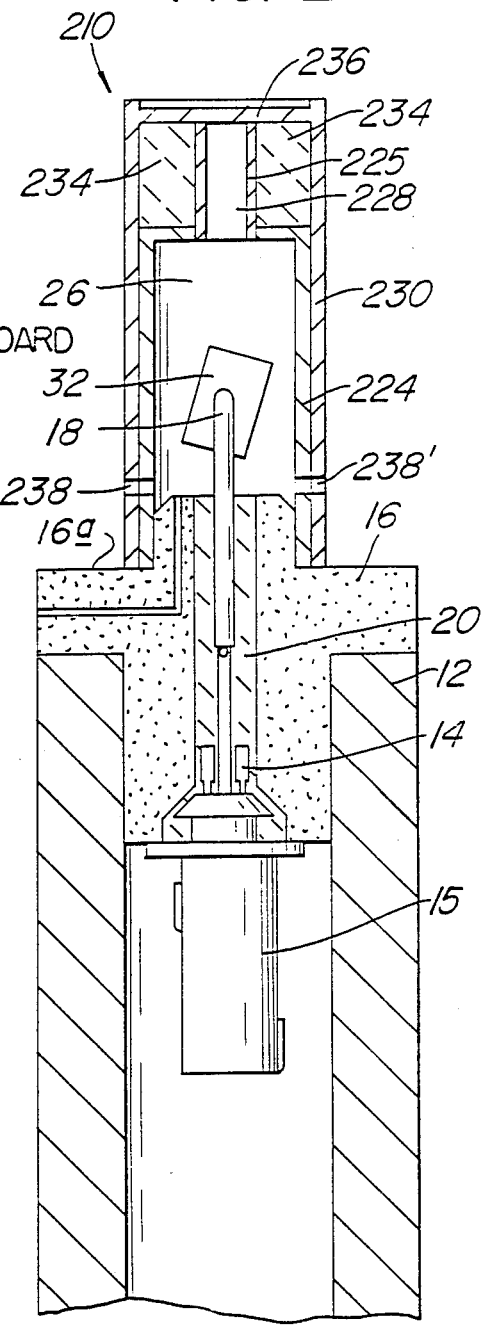

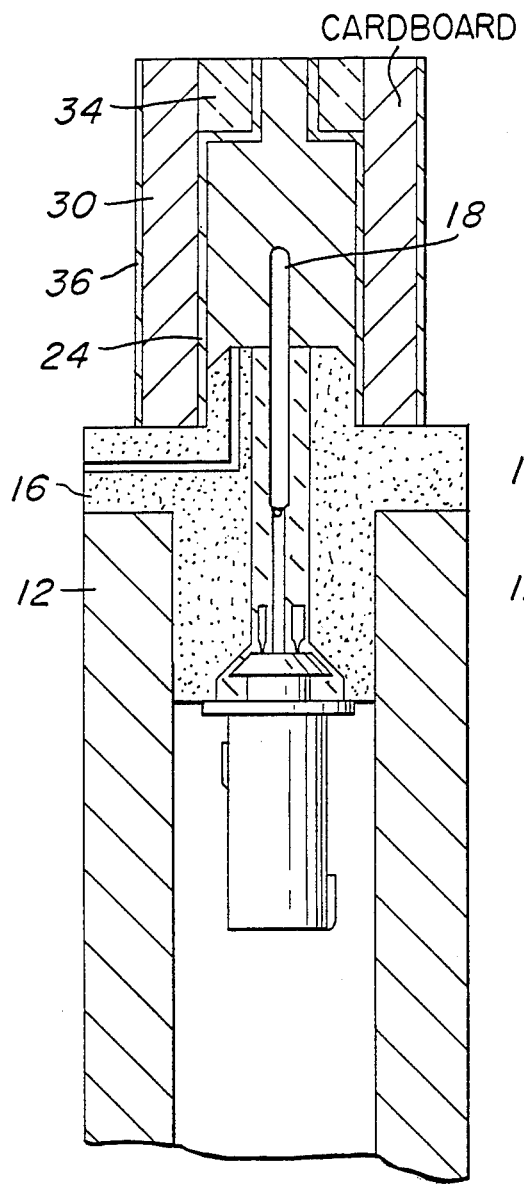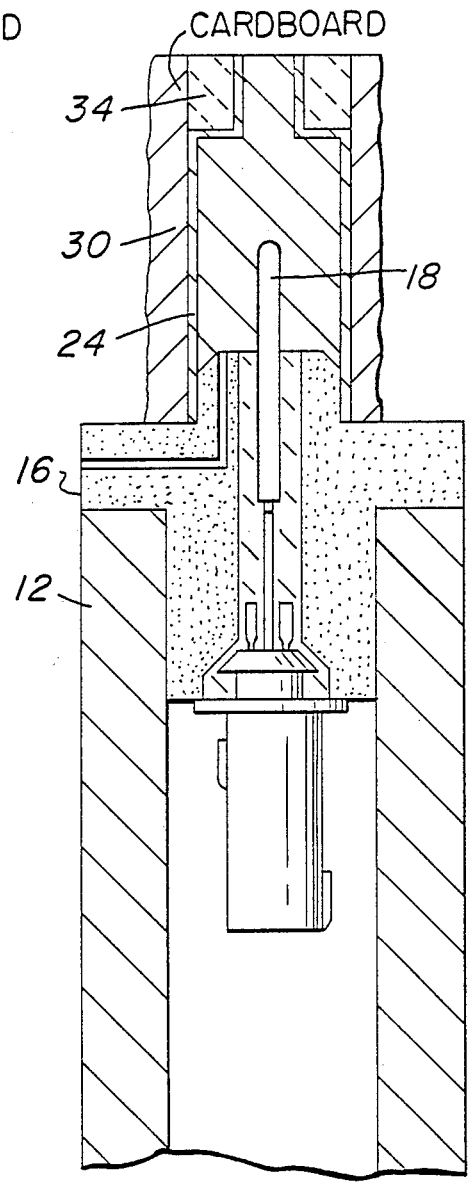

FIG. 4c
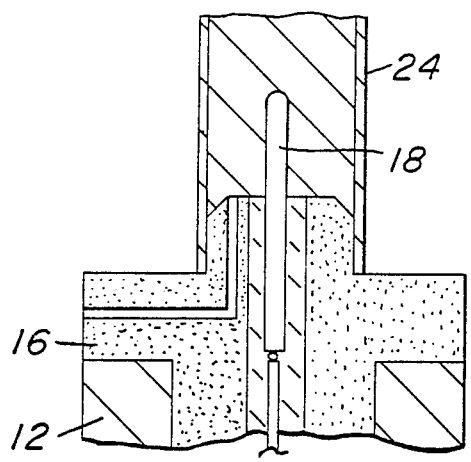
FIG. 4d
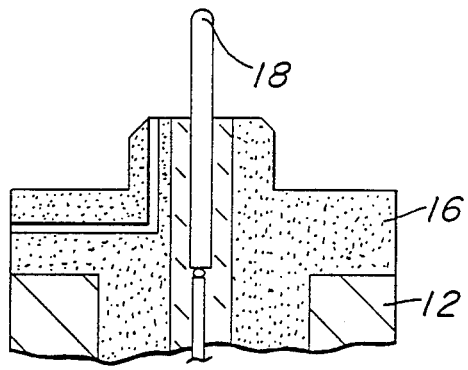
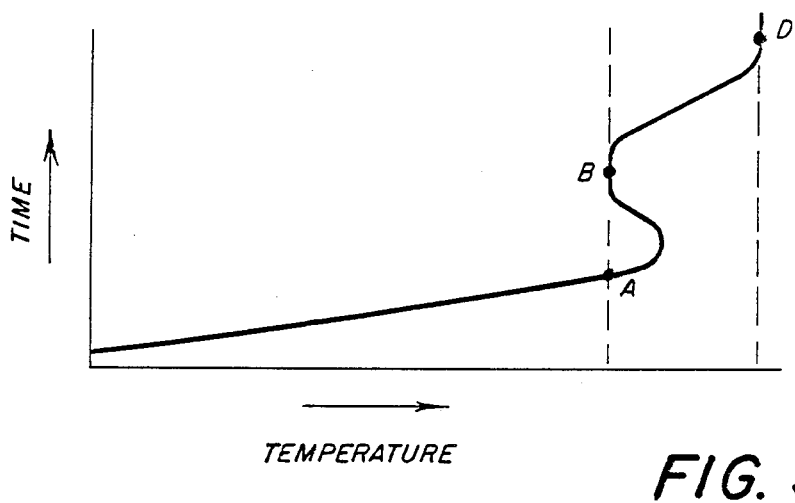
FIG. 5

TWO TEMPERATURE MEASURING PROBE

This application is a continuation application of Ser. No. 929,232, filed Nov. 10, 1986, now abandoned and is related to simultaneously filed application Ser. No. 929,231, titled "Solidification Device" now abandoned.

BRIEF SUMMARY OF THE INVENTION

This invention relates to an immersion probe type device for the determination of the temperature of molten metal using a single thermocouple element. In particular, this invention relates to an expendable measuring probe which first measures the liquidus arrest temperature of a sample of molten metal bath and then, by use of a remelt chamber, exposes the thermocouple to the molten metal bath for determination of the bath temperature.

BACKGROUND OF THE INVENTION

The measurement of temperature during the refining or processing of metals is a common requirement throughout the industry. A measurement of the liquidus arrest temperature (i.e., the temperature at which the molten metal begins to solidify) is important for determining the analytic content of the metal alloy in the bath prior to pouring or casting of the metal. In particular such temperature measurements can be correlated to the level of carbon in cast irons or steels. In many applications, the measurement of both the molten metal temperature in the bath and the phase change temperature is desirable.

Typical measuring probes which measure both the bath and the phase change temperature consist of two separate thermocouple elements. One thermocouple element is exposed to the molten bath while the second thermocouple element, contained within a defined chamber, is exposed to a sample of both as it initiates a phase change from the molten state. Such probes require not only two thermocouple elements but also include additional hardware and electrical connections. Additionally, since two separate temperatures are being measured substantially simultaneously, the components which record and register the separate temperatures require separate read out portions. By doubling the structural and the operational requirements, additional cost is added to the production and operation of a two temperature measuring device.

SUMMARY OF THE INVENTION

The probe of the present invention is generally mounted on an elongated insulating support tube, typically made of a cardboard material. The support tube is closed at its immersion end by the probe. The probe of the invention generally consists of a body portion and a chamber portion. The body portion is preferably formed from a refractory material such as a resin coated molding sand or a ceramic type material. A thermocouple element supported on and extending away from the body portion of the probe is electrically connected adjacent to its supported end to cold contact joints. The cold joints are maintained within the body of the probe by a refractory cement which also supports the thermocouple element on the body portion. The cold joints are connected to electrical connectors which extend into the support tube where connection is made with the external wiring system. A housing extends beyond the end of the body portion opposite the cardboard tube. This housing defines a chamber around the thermocouple element. Means is provided for introduction of the molten metal into the chamber upon immersion of the probe into the bath. This introduction means may include a fill tube on the top of the housing having a cap sealing its end. The cap prevents the slag on top of the bath from entering the chamber on initial immersion. Continued exposure of the cap to the molten metal environment causes the cap to be consumed into the bath, opening the end of the fill tube. Means is also provided for evacuating air from the chamber as it is filled with molten metal.

After immersion of the probe into the bath, the protective cap is consumed by the molten metal and the open end of the fill tube is exposed. A sample of the molten metal flows into the chamber through the fill tube or other introduction means and is chilled by the mass of the housing. The housing may include a metal lining when a high rate of sample chilling is desired. The thermocouple element inside the chamber detects the temperature of the molten metal sample as it is cooled. The sample temperature is monitored until the metal begins to solidify. During the time needed to detect the temperature at which this phase change occurs, the outside protection of the housing is progressively consumed by the molten metal bath. The consumption of the housing may include any number of mechanical or chemical reactions with the bath metal, including, but not limited to melting, charring, actual destruction of the housing form or dissolving. Upon complete or partial consumption of the housing the solidified portion of the sample is exposed directly to the molten metal bath environment. This sample then remelts into the bath and the thermocouple element may then measure the actual molten bath temperature. During remelt of the sample, the reverse phase change temperature may be detected to verify the first alloy determination corresponding to the liquids arrest curve.

Further advantages of this invention will become apparent to those skilled in the art by describing the preferred embodiment of this invention.

For the purpose of illustrating the invention, there is shown in the drawings forms which are presently preferred; it being understood; however, that this invention is not limited to the precise arrangements and instrumentalities shown.

BRIEF DESCRIPTION OF THE DRAWINGS

FIG. 1 shows a cross section of one embodiment of the invention.

FIG. 2 shows an alternate embodiment of the invention from that shown in FIG. 1.

FIGS. 4a, 4b, 4c, 4d show a measuring probe of the invention during various stages of immersion in a metal bath.

FIG. 5 is a graph of temperature versus time of the measuring probe illustrated in FIG. 4.

DETAILED DESCRIPTION OF THE PREFERRED EMBODIMENTS

Figure 3:
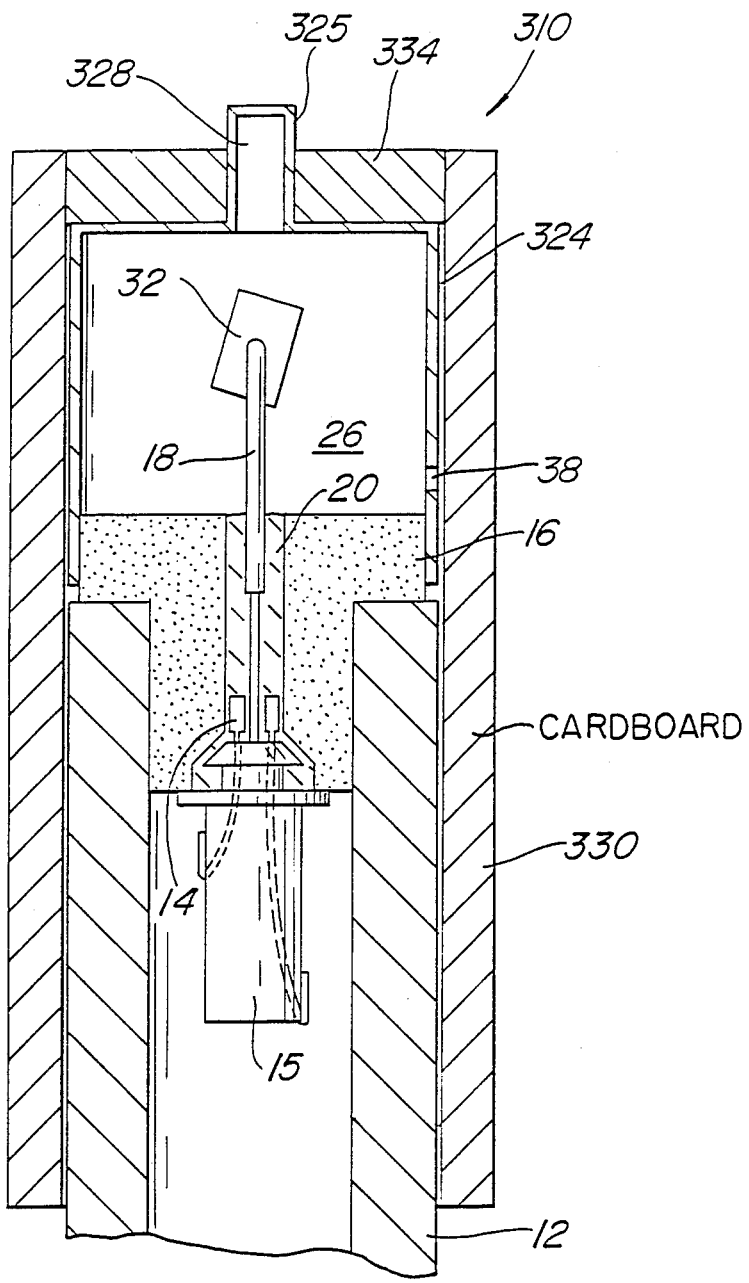
FIG. 3 shows an alternate embodiment of the invention from that shown in FIGS. 1 or 2.

A measuring probe 10, as shown in FIG. 1, is supported on a hollow support tube 12, which is typically made of a cardboard or paper board material. The measuring probe 10 is inserted into the immersion end of the hollow tube 12. The tube protects the electrical connector 15 of the probe 10 which is used to make electrical connection with external instrumentation (not shown).

The probe 10 includes a body portion 16 which may be typically formed from a ceramic material or a resin coated molding sand. A thermocouple element 18 is mounted on an extends away from the body 16 in the opposite direction of the support tube 12. The thermocouple wires of the element 18 are connected electrically through a refractory cement 20 within the body portion 16 and attached to the electrical connector 15 through the compensating leads 14. The refractory cement 20 seals the body portion 16 and supports the thermocouple element 18 on the probe 10.

Mounted on body 16 is a housing 24 which surrounds the thermocouple element 18 and defines a solidification chamber 26. One end of the housing 24 abuts against the body 16 and may be maintained in a fixed position by a shoulder 16a or by the refractory cement 20. An entry port 28 is provided on the housing 24 which permits the molten metal of the bath to enter the chamber 26 upon immersion of the probe 10. The housing 24 is preferably made of metal which will serve as a chill material for soldifying the sample of molten metal which enters the chamber 26. However, a variety of materials may be used as long as the molten metal is first chilled to induce the phase change of the bath sample and then, due to exposure to the bath environment is consumed into the bath. A ceramic material which either melts or breaks apart upon extended exposure to the metal bath may also be used for this housing.

The entry port 28 to the chamber 26 in FIG. 1 is in the form of a fill tube 25 positioned at the top of the housing 24. This fill tube 25 is, preferably, made of the same material as an integrally formed with the housing 24. Surrounding the periphery of the housing 24 in FIG. 1 is a sleeve 30 which acts to initially insulate the external portion of the housing 24 prior to complete consumption of the sleeve 30 which then induces direct contact of the housing 24 with the bath. Sleeve 30, which is typically a cardboard material, extends from the body portion to a position above the top of the housing 24. The annular space between the extension of the sleeve 30 and the fill tube 25 is filled with a refractory cement 34 (or a resin sand).

A portion of tube 25 extends above the cement 34 and is closed, prior to immersion, by a top cap 36. The cap 36 protects the chamber 26 during initial immersion through the slag at the top of the molten bath.

Chamber 26 is provided with a deoxidant material 32 for deoxidizing the bath sample during the solidification process. This material 32 is typically a predetermined amount of aluminum.

The embodiment in FIG. 2 differs from that in FIG. 1 in that the fill tube 225 is not made of the same material as the housing 224. The tube 225 is positioned within the cement 234 at the top of the housing 224 to provide the initial access to the chamber 26 for the molten metal of the bath. Also included in this embodiment are a plurality of exhaust ports 238 which are provided at the base of the housing 224 adjacent to the body portion 16.

These ports 238 provide an entrance port to the chamber 226 and an exhaust port for the gases contained within the chamber 226 prior to the immersion or the gases which are generated during deoxidation of the sample or consumption of the housing.

The exhaust ports 238 in FIG. 2 should be compared to vent hole 38 shown in FIGD. 1 and 2. Vent hole 38 also permits the exhaust of gases from the chamber, away from the area within the support tube 12. This vent hole 38 is a defined passage through body portion 16.

FIG. 3 shows another embodiment of the invention from that shown in either FIGS. 1 or 2. The probe 310 in FIG. 3 includes a housing 324 which may be of either construction shown in FIGS. 1 or 2. The housing 324 is protected by sleeve 330 which extends from a position even with the end of the fill tube 328 to wrap around the support tube 12. The cement fill 334 covers the area between the sleeve 330 and fill tube 325 as seen in both previously described embodiments. A cap (not shown) similar to caps 36 and 236 may also be provided to close the fill tube 325 and entry port 328 during initial immersion.

The method of using the probe 10 will be described hereafter. Although it should be noted that probes 210 and 310 function in substantially the same manner.

As shown in FIG. 4a, a few seconds after immersion of the probe 10 into the molten metal bath, the protective cap 36 will be consumed by the bath, exposing the fill tube 25 and opening entry port 28. The molten metal from the bath substantially fills the chamber 26 and consumes the deoxidant material 32. The gas displaced by the incoming metal is exhausted through vent hole 38 (or exhaust ports 238). This exhaustion of the gas in the chamber 26 is desirably directed into the bath rather than into the interior of the cardboard tube 12 so as to avoid the formation of deposits on the electrical contacts 15 or their electrical connections. However, these contacts 15 may be protected in any convenient manner as desired. The sample of the bath is chilled by the housing 24 and begins to solidify. During cooling of the sample, the thermocouple element 18 inside the chamber 26 detects the phase change temperature of the sample. The thermocouple 18 is electrically connected from the cold compensating leads 14 and the electrical contacts 15 through the support tube 12 to a recorder (not shown). The recorder indicates the temperature of the sample during the phase change. The initial phase change temperature of the sample can be correlated to a specific carbon or alloy content of the molten metal bath. FIG. 5 shows a trace of the temperature seen by the thermocouple 18 versus time of immersion. The initial phase change temperature is indicated as point B on this curve.

After immersion and during the phase change detection period, the cardboard sleeve 30 is consumed by the molten bath (FIG. 4b). The time required to consume the sleeve 30 should be longer than the time to measure the phase change temperature of the sample. The thickness of sleeve 30 should be proportional to the cooling rate of the metal in the chamber 26 so that the chamber remains intact long enough to obtain the desired liquidus arrest temperature. The sleeve 30 insulates the housing 24 while the solidification of the sample takes place.

Once the sleeve 30 is completely consumed, the housing 24 is exposed to the bath and will begin to be consumed so as to also expose the sample to the bath environment (FIG. 4c). The partially solidified sample then remelts into the bath and the thermocouple 18 is expose directly to the bath (FIG. 4d). The device functions as a typical bath temperature sensing probe and will detect the actual temperature of the bath (point D, FIG. 5). During remelt of the sample, the reverse phase change temperature (point B in FIG. 5) may be detected by the recorder such that the previous carbon or alloy content determination may be verified.

It is important to note that the structure of the remainder of the measuring probe 10 must be such that the probe body 16 and its internal electrical connections are maintained through the completion of the solidification and bath temperature measurements.

The housing 24 and sleeve 30 may be made of any numerous combinations of materials or in a variety of forms. The only limitation is the maintenance of the electrical contacts 14 and the thermocouple 18 for the period of time required to produce and measure the desired phase change temperature of the sample. The size and proportions of the housing 24 will depend upon the chill rate of the metal on the sample. The desired thickness of the housing and cardboard sleeve will depend on the thermal conductivity of these parts, such that the solidification process may take place within the chamber.

The present invention may be embodied in other specific forms without departing from the spirit or essential attributes thereof and, accordingly, reference should be made to the appended claims, rather than to the foregoing specification, as indicating the scope of the invention.

I claim:

1. A process for determining the alloy content of a molten metal mixture in a bath comprising the steps of: immersing a measuring probe into the molten metal bath; taking a sample portion of the bath into a chamber of said probe; chilling the sample portion within said chamber measuring and recording the liquidous arrest temperature of the sample portion with a single thermocouple element positioned within said chamber; exposing the sample portion to the bath; remelting the sample portion; measuring and recording the molten metal bath temperature with said single thermocouple element after remelt of the sample portion; and correlating the liquidous arrest temperature measurement to a known alloy content of the bath.

2. An immersion probe for measuring the phase change temperature and bath temperature of molten metal in a bath, comprising: a body portion; a single means for measuring the bath temperature and phase change temperature of the molten metal; chamber means for receiving a sample of the molten metal, said temperature measuring means positioned within said chamber means, said chamber means further including a wall adapted to chill the sample to at least the initiation of solidification of the sample such that said measuring means detects the phase change temperature of the sample, said chamber means being consumed by the molten metal after initiating solidification of the sample to expose the sample to the molten metal, to remelt the sample and to expose the temperature measuring means to the molten metal for direct measurement of the temperature of the molten metal; and means for recording the measured temperature.

3. A probe as claimed in claim 2 wherein said body portion further comprises:
a formed section adapted for insertion into a hollow support tube and defining an aperture therethrough adapted for exhaust from said chamber; a first cement fill supporting said measuring means said chamber means on said body section, said chamber means comprising a housing supported by said body portion and having a top, said housing defining a chamber around said measuring means, said housing having an aperture for admittance of the molten metal sample into the chamber upon immersion of the probe into the molten metal and means for exhaustion of gas from said chamber during entry of the molten metal into said chamber.

4. A probe as claimed in claim 3 further comprising: means for temporarily delaying the admittance of the molten metal sample into the chamber upon initial immersion of the probe into the molten metal.

5. A probe as claimed in claim 3 wherein said housing includes a metal wall which causes the chilling of the molten metal sample in the chamber.

6. A probe as claimed in claim 5 further comprising:
a consumable insulating protective sleeve surrounding the periphery of said housing;
a fill tube positioned adjacent to said aperture on the top of said housing;
a fill material provided between said sleeve and said fill tube above the top portion of said housing.

7. A probe as claimed in claim 6 further comprising:
a pipe surrounding the periphery of said sleeve protecting said sleeve during initial immersion of the probe into the molten metal; and
a cap closing said fill tube for delaying entry of molten metal into said chamber during initial immersion of the probe into the molten metal.

8. A measuring probe for determining the phase change temperature and bath temperature of molten metal in a bath comprising:
a body portion adapted to be supported by a hollow support tube, said body portion supporting a housing having a top and a thermocouple, said thermocouple extending into a chamber formed by said housing and said body portion, said housing having entry means adapted for admittance of a sample of molten metal into the chamber after immersion of the probe into the molten metal bath, said housing further including a wall adapted to chill the sample such that the thermocouple measures the phase change temperature of the molten metal sample which is recorded, said wall of said housing being of such material so as to be consumed by the bath within a time in excess of the time required to determine the phase change temperature of the sample and, upon consumption, exposing the sample to the molten metal for remelting the sample and the same thermocouple measuring the molten metal bath temperature after the remelting of the sample which is recorded.

9. A probe as claimed in claim 8 further comprising:
an insulating protective sleeve surrounding the periphery of said housing, said sleeve being consumed by the molten metal prior to the consumption of said housing by the molten metal and said entry means further comprising a fill tube mounted on the top portion of said housing, said fill tube being closed by a protective cap which is consumed by said molten metal immediately after initial immersion of the probe into the molten metal, said cap protecting the internal portion of said housing during initial immersion.

10. A process for measuring both the phase change temperature and the bath temperature of a molten metal by means of a single thermocouple element positioned within a chamber of a measuring probe comprising the steps of: immersing said measuring probe into a molten metal bath; taking a sample of the molten metal bath into said chamber; detecting the liquidous arrest temperature of the sample with said single thermocouple element; exposing the sample to the molten metal bath for remelting the sample into the bath; measuring the bath temperature with said single thermocouple element after remelting the sample and recording the measured temperatures.

11. A process for measuring as claimed in claim 10 further comprising the steps of: chilling the sample by means of a housing which is consumable in the molten metal bath.

12. A process for measuring as claimed in claim 10 further comprising the step of: detecting the phase change temperature during remelting of the sample.

* * * * *